United States Patent [19]

Kovacs et al.

[11] Patent Number: 5,283,328

[45] Date of Patent: Feb. 1, 1994

[54] 1-TRIACONTANOL DERIVATIVES

[75] Inventors: Antal Kovacs; Andras Liptak; Pal Nanasi; Zoltan Szurmai; Istvan Csernus; Katalin Marossy; Katalin Kovacs-Hadadi; Zsuzsa Emri-Harsi; Ildiko Gombos-Nemeti, all of Debrecen, Hungary

[73] Assignee: Biogal Gyogyszergyar Rt., Debrecen, Hungary

[21] Appl. No.: 768,234

[22] PCT Filed: Dec. 18, 1990

[86] PCT No.: PCT/HU90/00082

§ 371 Date: Oct. 11, 1991

§ 102(e) Date: Oct. 11, 1991

[87] PCT Pub. No.: WO91/09044

PCT Pub. Date: Jun. 27, 1991

[30] Foreign Application Priority Data

Dec. 18, 1989 [HU] Hungary ............... 6646/89

[51] Int. Cl.$^5$ ............................................. C07H 15/04
[52] U.S. Cl. ...................................... 536/120; 536/4.1
[58] Field of Search ................... 536/120, 124, 18.6; 568/619, 606, 618

[56] References Cited

U.S. PATENT DOCUMENTS

| | | | |
|---|---|---|---|
| 4,713,447 | 12/1987 | Letton | 536/18.6 |
| 4,847,368 | 7/1989 | Lueders et al. | 536/120 |
| 4,990,605 | 2/1991 | Lueders | 536/120 |
| 4,996,306 | 2/1991 | McDaniel et al. | 536/120 |

FOREIGN PATENT DOCUMENTS 45-20097 7/1970 Japan.
60-174796 9/1985 Japan.

OTHER PUBLICATIONS

Packer, L., Toxicity, Antioxidants, and Metabolism, Molecular Basis of Membrane-Associated Diseases, pp. 335-343, Springer-Verlag, Berlin (1989).
D. Harman, "The Free Radial Theory of Aging", Clinical Aspects of Vitamin E, pp. 385-393 (Elsevier Science 1987).
Clinical Science and Molecular Medicine, 47, pp. 215-222 (1974).
Mechanisms of Aging and Development, 14, pp. 245-251 (Elsevier 1980).
Archives of Disease in Childhood, pp. 748-757, vol. 63 (1988).
Preventive Medicine, vol. 18, pp. 553-561 (1989).
Cancer Research, vol. 49, issued Aug. 1, 1989, Tietze et al, "Proton-Medicated Liberation of Aldophosphamide from a Nontoxic Prodrug: A Strategy for Tumor-selective Activation of Cytocidal Drugs", pp. 4179-4184.

Primary Examiner—Johnnie R. Brown
Assistant Examiner—Everett White
Attorney, Agent, or Firm—Herbert Dubno; Jonathan Myers

[57] ABSTRACT

The present invention relates to compounds of the formula I $$[CH_3-(CH_2)_{29}-O-]_m-R \qquad (I)$$

wherein
if m stands for 1, then
R represents a group derived from a mono- or di- or oligosaccharide by removing the hydrogen atom from the hydroxyl group being in the 1(alpha) or 1(beta) position, or the O-protected, preferably acetylated derivative thereof,
if m stands for 2, then
R represents a group derived by removing a hydrogen atom attached to the carbon atom being in position 1 of the reaction product of glucose and mono-, di- or triethylene glycol or the O-protected, preferably O-acetylated derivative thereof.

3 Claims, No Drawings

1-TRIACONTANOL DERIVATIVES

CROSS REFERENCE TO RELATED APPLICATIONS

This application is a national phase of PCT/HU90/00082 filed Dec. 18, 1990 and based upon Hungarian National Application 6646/89 filed Dec. 18, 1989.

FIELD OF THE INVENTION

The present invention relates to novel 1-triacontanyl glycosides of formula I $$[CH_3-(CH_2)_{29}-O-]_m-R \quad (I)$$

wherein
m is 1 or 2 and
if m stands for 1, then
R represents a group derived from a mono- or di- or oligosaccharide by removing the hydrogen atom from the hydroxyl group being in the 1(alpha) or 1(beta) position, or the O-protected, preferably acetylated derivative thereof,
if m stands for 2, then
R represents a group derived by removing a hydrogen atom attached to the carbon atom being in position 1 of the reaction product of glucose and mono-, di- or triethylene glycol or the O-protected, preferably O-acetylated derivative thereof.

The compounds of formula I of the invention are biologically active compounds and they are especially useful for the prevention and treatment of different diseases connected to aging.

BACKGROUND OF THE INVENTION

1-Triacontanol, the primary alcohol having 30 carbon atoms, was separated and identified by Chibnall in 1933.

According to U.S. Pat. No. 4,150,970, 1-triacontanol is a growth regulator for plants. This activity is also supported by Science, Vol. 195, pages 1339 to 1341.

According to published European patent application No. 78,533 a topical pharmaceutical composition comprising 1-triacontanol as active ingredient is useful for treating skin disorders.

No reference has been made so far to the different sugar derivatives of 1-triacontanol.

The use of 1-triacontanol and the examination of the mechanism of its activity is very difficult as this compound is highly lipophylic and hardly dissolves in water.

OBJECT OF THE INVENTION

It is an object of the invention to provide improved 1-triacontonyl compounds free from drawbacks of earlier 1-triacontonyl compounds.

DESCRIPTION OF THE INVENTION

We have found that the 1-tricontanol glycosides, according to the present invention dissolve well in water and have a less apolar character. The compounds have the formula I as defined above.

DETAILED DESCRIPTION OF THE INVENTION

In the description under the term "monosaccharide" the aldopentoses and aldohexoses are understood. When, in the formula I, m is 1, then the group derived from a monosaccharide by removing the hydrogen atom from the hydroxyl group being in the 1(alpha) or 1(beta) position may be a ribosyl, arabinosyl, xylosyl, lixosyl, allosyl, altrosyl, glucosyl, mannosyl, gulosyl, idosyl, galactosyl, talosyl group from which the glucosyl group is preferred.

The protected derivatives thereof may be such groups wherein one or more, preferably all of the free hydroxy groups are substituted by a conventional protecting group. The most preferred protecting group is the acetyl group. The most preferred protected monosaccharide residue represented by R when m=1 is glucosyl tetraacetate.

Under the term "oligosaccharides" the bioses, such as lactose, genciobiose, laminaribiose, maltose, cellobiose and the maltoligomers, such as maltotriose, maltotetraose, maltopentaose, maltohexaose, maltoheptaose, maltooctaose are understood. When m is 1, then the group derived from an oligosaccharide by removing the hydrogen atom from the hydroxyl group being in the 1(alpha) or 1(beta) position is preferably lactosyl, cellobiosyl, maltosyl, maltotriosyl, maltotetraosyl, matopentaosyl, maltohexaosyl, maltoheptaosyl or maltooctaosyl group.

The protected derivatives thereof may be such groups wherein one or more, and preferably all of the free hydroxy groups are substituted by a conventional protecting group. The most preferred protecting group is the acetyl group. The most preferred acetylated oligosaccharide residues represented by R when m=1 are cellobiosyl heptaacetate, lactosyl heptaacetate, maaltosyl heptaacetate, maltotriosyl decaacetate, maltotetraosyl tridecaacetate, maltohexaosyl nonadecaacetate, and maltoheptaosyl docosaacetate.

Thus a preferred group of compounds of formula I is that wherein
m is 1 and
R represents an aldopentosyl, aldohexosyl, biosyl or oligomaltosyl group or the acetylated derivative thereof. A more preferred group of compounds of formula I is wherein
m is 1 and
R represents glucosyl, lactosyl, cellobiosyl, maltosyl or oligomaltosyl group or the acetylated derivative thereof. The most preferred group of formula I is wherein
m is 1 and
R represents glucosyl, lactosyl, cellobiosyl, maltosyl, maltotriosyl, maltotetraosyl, maltopentaosyl, maltohexaosyl, maltoheptaosyl, maltooctaosyl, glucosyl tetraacetate, cellobiosyl heptaacetate, lactosyl heptaacetate, maltosyl heptaacetate, matotriosyl decaacetate, maltotetraosyl tridecaacetate, maltopentaosyl hexadecaacetate, maltohexaosyl nonadecaacetate; maltoheptaosyl docosaacetate, maltooctaosyl pentacosaacetate. Another preferred group of formula I is wherein
m is 2 and
R represents 1,8-di-(beta-D-glucopyranos-6-yloxy-1-yl)-3,6-dioxaoctane, 1,5-di-(beta-D-glucopyranos-6-yloxy-1-yl)-3-oxapentane, 1,2-di-(beta-D-glucopyranos-6-yloxy-1-yl)-ethane, 1,8-di-(2,3,4-tri-O-acetyl-beta-D-glucopyranos-6-yloxy-1-yl)-3,6-dioxaoctane, 1,5-di-(2,3,4-tri-O-acetyl-beta-D-glucopyranos-6-yloxy-1-yl)-3-oxapentane, 1,2-di- (2,3,4-O-acetyl-beta-D-glucopyranos-6-yloxy-1-yl)-ethane.

Acute toxicity

The acute toxicity of the compounds according to Examples 1 to 21 was determined by using Turner's method (1965) on CFLP mice by oral administration. The results were evaluated by Litchfield-Wilcoxon's graphic method (1949). The $LD_{50}$ value of all of the compounds of the invention was higher than 10 g/kg. That means that the compounds of the invention are not toxic.

Free radical scavenger activity

The free radical scavenger activity of the compounds of the invention was examined by the in vitro method of Imre Zs.-Nagy (Mech. Ageing Dev., 14, pages 245-251, 1980), i.e. the peptide polymerizing effect of —OH free radicals formed in the modified Fenton-reaction was examined in the presence of the compounds of the invention. Centrofenoxine (dimethylamino ethanol) and 1-triacontanol were used as comparative compounds.

According to the experiments the free radical scavenger activity of 1-triacontanyl-maltoheptaoside (THM) significantly exceeds that of centroferoxine. In a concentration of 0.6 mmole THM was effective, while at the same concentration centrofenoxine was already ineffective. 1-Triacontanol was also not effective in the same concentration.

Antioxidant activity

The antioxidant activity of the compounds of the invention was examined on the basis of the in vitro test worked out by Stocks et al. (Clin. Sci. Mol. Med. 215-222, 223-233, 1974). In the above test the $C_{50}$ value (that concentration which is necessary to reduce the initial autooxidation with 50%) of the compounds was measured. The $C_{50}$ value is characteristic for the antioxidant properties of the compound; the less is $C_{50}$ the better radical scavenger the compound is. In the test THM inhibited the lipidperoxidation depending on its dose, its $C_{50}$ value (that concentration which is necessary to reduce the initial autooxidation with 50%) was 0.56 mM.

According to the test results the comparative compounds did not influence the lipidperoxidation. At a concentration of 0.66 mM they reduced the initial autooxidation to an extent of less than 25%.

The $C_{50}$ value of vitamine E, which is generally used in therapy against pathological free radical reactions, is 0.45 mM.

The advantage of the compounds of the invention over vitamin E is that they are water and lipid soluble, while vitamin E is only lipid soluble.

The novel compounds of formula I are useful for the prevention or treatment of different diseases, especially those diseases which are connected to aging. Their significance is enhanced by the fact that the novel glycosides are not toxic, exert their activity at a low concentration and not only lipid but also water soluble.

Dosage forms suitable for internal administration contain from about 1 milligram to about 500 milligrams of active ingredient per unit. The dosages administered vary depending upon known factors such as the mode and route of administration, age, health and weight of the recipient; nature and extent of symptoms, kind of concurrent treatment, frequency of treatment, and the effect desired. In the oral and topical pharmaceutical compositions the active ingredient will ordinarily be present in an amount of about 0.5 to 95% or 0.01 to 1% by weight, respectively based on the total weight of the composition.

The pharmaceutical compositions comprising the compounds of the invention as active ingredient can be administered via any of the accepted modes of administration for therapeutic agents. These methods include oral, parenteral, transdermal, rectal, subcutaneous and other systemic modes. When the intended route of administration is parenteral, the pharmaceutical composition should, of course, be in a sterile form.

Thus the compositions may be in the form of solid dosage forms such as capsules, tablets, coated tablets, powders, suppositories, ointments or liquid dosage forms such as syrups, emulsions, injections, elixirs, suspensions, emulsions, etc.

For solid compositions, conventional non-toxic solids include, for example, pharmaceutical grades of mannitol, lactose, starch, magnesium stearate, sodium saccharin, talcum, cellulose, glucose, sucrose, magnesium carbonate, and the like may be used. The active compound may be formulated as suppositories using, for example, polyalkylene glycols, such as propylene glycol, as a carrier.

Liquid dosage forms can, for example, be prepared by dissolving, dispersing, suspending, emulsifying, etc. an active compound and optional pharmaceutical adjuvants in an excipient, such as, for example, water, saline, aqueous dextrose, glycerol, ethanol and the like.

If desired, the pharmaceutical composition may also contain minor amounts of nontoxic auxiliary substances such as wetting agents, pH buffering agents, preservatives, flavoring agents, etc., for example, sodium cetate, sodium lauryl sulphate, sorbitan monolaurate, triethanolamine sodium acetate, triethanolamaine oleate, etc. Actual methods of preparing such dosage forms are known, or will be apparent, to those skilled in the art; see Remington's Pharmaceutical Sciences, Mack Publishing Company, Easton, Pa., 15th Edition, 1975.

The compounds of formula I are prepared by reacting 1-triacontanol with the bromine derivative of the appropriate protected, preferably acetylated derivative of the corresponding saccharide (when m=1) or with the bromine derivative of the corresponding protected, preferably acetylated crown-ether (when m=2) preferably in the presence of a catalyst in an inert solvent or solvent mixture, then if desired, removing the protecting group(s).

In the course of glycosylation, the acetylated sugar can be used in a molar amount of 0.7-1.3 calculated for 1 mole of 1-triacontanol.

The reaction can be carried out at a temperature of 20°-80° C., preferably at 50°-60° C.

The glycosylation of 1-triacontanol in the generally suggested neutral solvents (e.g. chlorinated hydrocarbons, acetonitrile, nitromethane, N-dimethylformamide, dimethyl sulfoxide) cannot be carried out due to the low solubility of 1-triacontanol. According to our experiments a mixture of toluene and nitromethane can preferably used in the reaction as solvent.

The reaction can be facilitated by the presence of a catalyst. As catalyst, preferably mercury bromide, silver oxide, silver carbonate or mercury cyanide, most preferably mercury cyanide can be used.

When the reaction is carried out in the mixture of toluene and nitromethane in the presence of a catalyst at a temperature of 60° C., the reaction can be completed within some hours.

At the end of the glycosylation the product thus obtained can be purified in a manner known per se, e.g. by recrystallization or column chromatography or the acetyl groups can be removed.

The removal of the acetyl groups can be carried out by conventional techniques, such as splitting off with the aid of sodium methylate.

The invention is further illustrated by the following, non-limiting examples.

EXAMPLE 1

1-Triacontanyl-tetra-O-acetyl-beta-D-glucopyranoside

From a mixture of 300 mg (0.94 mmoles) 6-triacontanol, 400 mg (1.583 mmoles) of mercury cyanide, 20 ml toluene and 20 ml of nitromethane the half of the solvent is distilled off under atmospheric pressure. The residue is cooled to a temperature of 60° C. and 411 mg (1 mmole) of alpha-acetobromo-D-glucose are added and the mixture is stirred for 5 hours at the same temperature.

Then the mixture is cooled to a temperature of 18°–20° C., 50 ml of butanol are added, the mixture is filtered and evaporated. The residue is taken up with 100 ml of toluene and the solution is washed with 2×30 ml of 5% by weight aqueous potassium iodide solution then with 2×30 ml of water. Then it is dried over sodium sulphate and evaporated. The crude product is recrystallized from ethyl acetate.

Yield: 220 mg (41.8%)
Melting point: 80° C.
$R_f$: 0.63 (in a 95:5 mixture of dichloromethane and acetone) $alpha^{20}{}_D = -5.1°$ C. (c=0.25; toluene)

EXAMPLE 2

1-Triacontanyl-beta-D-glucopyranoside 150 mg of product prepared according to the previous example are suspended in a mixture of 15 ml of methanol and 15 ml of n-butanol. Then 10 mg of sodium methylate are added and the reaction mixture is boiled for 5 hours. The hot solution is neutralized with the aid of Amberlite IR-120 (H+) resin, filtered then evaporated after cooling. The desacetylated product is crystallized from methanol.

Yield: 100 mg (85.3%)
Melting point: 94° C.

EXAMPLE 3

1-Triacontanyl-hepta-O-acetyl-beta-cellobioside 300 mg (0.94 mmoles) of 1-triacontanol are reacted with alpha-acetobromo cellobioside and worked up according to the method described in Example 1. The prooduct is crystallized from ethyl acetate.

Yield: 407 mg (56.3%)
Melting point: 120°–128° C.
$R_f$: 0.34 (in a 95:5 mixture of dichloromethane and acetone) $alpha^{20}{}_D = -15.6°$ (c=0.28; toluene)

EXAMPLE 4

1-Triacontanyl-beta-cellobioside 300 mg of product obtained in the previous example are desacetylated in a mixture of 303 ml of methanol and 30 ml of n-butanol according to the method described in Example 2. The product is crystallized from 20 ml of methanol.

Yield: 195 mg (90.1%)
Melting point: 128°–138° C.

EXAMPLE 5

1-Triacontanyl-hepta-O-acetyl-beta-lactoside 300 mg (0.94 mmoles) of 1-triacontanol are reacted with alpha-acetobromo lactose and worked up according to the method described in Example 1. The product is purified by column chromatography (column: Kieselgel 0.063–0.2 mm; eluent: a 85:15 mixture of dichloro methane and acetone).

Yield: 571 mg (61%)
$alpha^{20}{}_D = -4.2°$ (c=0.57; toluene)

EXAMPLE 6

1-Triacontanyl-beta-lactoside 300 mg of product obtained in the previous example are desacetylated in a mixture of 30 ml methanol and 30 ml of n-butanol according to the method described in Example 2. The product is crystallized from methanol.

Yield: 190 mg (87.8%)
Melting point: 166°–170° C.

EXAMPLE 7

1-Triacontanyl-hepta-O-acetyl-beta-maltoside 106.2 mg (1.3 mmoles) of 1-triacontanol are reacted with 200 mg of alpha-acetobromo-maltose in accordance with Example 1. The crude product is purified by column chromatography (column: Kieselgel 0.063–0.2 mm; eluent: a 2:2:1 mixture of toluene, dichloro methane and acetone). The glycoside acetate thus obtained is recrystallized from methanol.

Yield: 157 mg (51.9%)
Melting point: 82°–87° C.
$alpha^{20}{}_D = +26.3°$ (c=0.22; toluene)
$R_f$: 0.74 (in a 2:2:1 mixture of toluene, dichloromethane and acetone)

EXAMPLE 8

1-Triacontanyl-deca-O-acetyl-beta-maltotrioside 318.7 mg (1 mmole) of 1-triacontanol are reacted with 840 mg of alpha-acetobromo-maltose in accordance with Example 1. The crude product is purified by column chromatography (column: Kieselgel 0.063–0.2 mm; eluent: a 2:2:1 mixture of toluene, dichloro methane and acetone). The glycoside acetate thus obtained is recrystallized from methanol.

Yield: 370 mg (32.8%)
Melting point: 77.79° C.
$alpha^{20}{}_D = +66.1°$ (c=0.29; toluene)
$R_f$: 0.63 (in a 2:2:1 mixture of toluene, dichloromethane and acetone)

EXAMPLE 9

1-Triacontanyl-beta-maltotrioside 300 mg of product obtained in the previous example are desacetylated in a mixture of 30 ml of methanol and 30 ml of n-butanol according to the method described in Example 2. The product is recrystallized from methanol.

Yield: 134 mg (64.9%)
Melting point: 88°–100° C.

EXAMPLE 10

1-Triacontanyl-trideca-O-acetyl-beta-maltotetraoside 218.7 mg (1 mmole) of 1-triacontanol are reacted with 1.0 g (0.783 mmoles) of alpha-acetobromo-maltotetraose according to Example 1. After working up the reaction mixture and separating the product by column chromatography the product is recrystallized from methanol.

Yield: 326 mg (25.5%)
Melting point: 81°–83° C.
$R_f$: 0.55 (in a 2:2:1 mixture of toluene, dichloromethane and acetone)
$\text{alpha}^{20}{}_D = +31.6°$ (c=0.22; toluene)

EXAMPLE 11

1-Triacontanyl-beta-maltotetraoside 400 mg of crude product obtained in the previous example are desacetylated in a mixture of 30 ml of methanol and 30 ml of n-butanol according to the method described in Example 2. The product is recrystallized from methanol.

Yield: 144 mg (54%)
Melting point: 80°–88° C.

EXAMPLE 12

1-Triacontanyl-hexadeca-O-acetyl-beta-maltopentaoside 225 mg (0.8 mmole) of 1-triacontanol are reacted with 1.05 g of alpha-acetobromo-maltopentaose according to Example 1. After working up the reaction mixture and separating the product by column chromatography the product is recrystallized from methanol.

Yield: 515 mg (39.9%)
Melting point: 76°–79° C.
$\text{alpha}^{20}{}_D = +71.6°$ (c=0.35; toluene)

EXAMPLE 13

1-Triacontanyl-beta-maltopentaoside 370 mg of product obtained in the previous example are desacetylated in a mixture of 30 ml of methanol and 30 ml of n-butanol according to the method described in Example 2. The product is washed with methanol and dried on air.

Yield: 234 mg (97.3%)
Melting point: 150°–158° C.

EXAMPLE 14

1-Triacontanyl-decosa-O-acetyl-beta-maltoheptaoside 219.4 mg (0.69 mmole) of 1-triacontanol are reacted with 1 mmole of alpha-acetobromo-maltoheptaose according to Example 1. The product is recrystallized from ethanol.

Yield: 250 mg (20%)
Melting point: 80° C.
$\text{alpha}^{20}{}_D = +75.9°$ (c=0.16; toluene)
$R_f$: 0.32 (in a 85:15 mixture of dichloromethane and acetone)

EXAMPLE 15

1-Triacontanyl-beta-maltoheptaoside 150 mg of product obtained in the previous example are desacetylated in a mixture of 50 ml of methanol and 50 ml of n-butanol according to the method described in Example 2. The product is recrystallized from methanol.

Yield: 57.5 mg (90.1%)
Melting point: 160°–168° C.

EXAMPLE 16

1-Triacontanyl-nonodeca-O-acetyl-beta-maltohexaoside 318.7 mg (1 mmole) of 1-triacontanol are reacted with 1.61 g (0.869 mmole) of alpha-acetobromo-maltohexaose according to Example 1. After working up the reaction mixture and separating the product by column chromatography the product is recrystallized from methanol.

Yield: 420 mg (21.9%)
Melting point: 82°–85° C.
$\text{alpha}^{20}{}_D = +71.9°$ (c=0.26; toluene)
$R_f$: 0.42 (in a 2:2:1 mixture of toluene, dichloromethane and acetone)

EXAMPLE 17

1-Triacontanyl-beta-maltohexaoside 450 mg of product obtained in the previous example are desacetylated in a mixture of 30 ml of methanol and 30 ml of n-butanol according to the method described in Example 2. The product is recrystallized from methanol.

Yield: 218 mg (75.8%)
Melting point: 163°–166° C.

EXAMPLE 18

1-Triacontanyl-pentacosa-O-acetyl-beta-maltooctaoside 318.7 mg (1 mmole) of 1-triacontanol are reacted with 2.28 mg (0.938 mmole) of alpha-acetobromo-maltooctaose according to Example 1. After working up the reaction mixture and separating the product by column chromatography the product is recrystallized from methanol.

Yield: 127 mg (4.9%)
Melting point: 103°–104° C.
$\text{alpha}^{20}{}_D = +76.9°$ (c=0.17; toluene)
$R_f$: 0.34 (in a 2:2:1 mixture of toluene, dichloromethane and acetone)

EXAMPLE 19

1-Triacontanyl-beta-maltooctaoside 100 mg of product obtained in the previous example are desacetylated in a mixture of 30 ml of methanol and 30 ml of n-butanol according to the method described in Example 2. The product is recrystallized from a small amount of methanol.

Yield: 44 mg (70.6%)
Melting point: 200°–206° C.

EXAMPLE 20

1,8-di-(triacont-1-yl-2,3,4-tri-O-acetyl-beta-D-gluocopyranos-6-yloxy)-3,6-dioxaoctane 760 mg (1.7 mmoles) of 1-triacontanol are dissolved in a mixture of 30 ml of dry toluene and 30 ml of nitromethane, then the mixture is evaporated to half its volume by azeotropic distillation. Then 525 mg (2.07 mmoles) of powdered mercury (II) cyanide and 670 mg (0.78 mmole) of 1,8-di(1-bromo-1-deoxy-2,3,4-tri-O-acetyl-beta-D-glucopyranos-6-yloxy)-3,6-dioxaoctane are added. The reaction mixture is stirred at a temperature of 60° C. for 2 hours. The two products detectable by thin-layer chromatography ($R_f$=0.56 and 0.14, respectively in a 9:1 mixture of dichloro methane and acetone) are separated by column chromatography and recrystallized from toluene.

Yield: 586 mg (38%)

Melting point: 76°–78° C.

$R_f$: 0.56 (in a 9:1 mixture of dichloromethane and acetone)

alpha$^{20}_D$ = −1.35° (c=0.148; toluene)

EXAMPLE 21

1,8-di-(triacont-1-yl-beta-D-glucopyranos-6-yloxy)-3,6-dioxaoctane 336 mg (0.21 mmole) of product obtained in the previous example are dissolved in a mixture of 40 ml of dry methanol and 20 ml of dry toluene and the mixture is stirred in the presence of catalytic amount of sodium methylate at a temperature of 50° C. The reaction mixture is neutralized with the aid of Amerlite IR-120 (H+) resin, filtered off and the filtrate is evaporated. The product is triturated with n-hexane, thus white, crystalline product is obtained.

Yield: 220 mg (78%)

Melting point: 89°–91° C.

alpha$^{20}_D$ = −62.49 (c=0.05; toluene)

EXAMPLE 22

| Tablet | |
|---|---|
| Compound of Example 9 | 10 mg |
| microcrystalline cellulose | 50 mg |
| corn starch | 20 mg |
| talcuum | 20 mg |
| | 100 mg |

Example 23

| Capsule | |
|---|---|
| Compound of Example 15 | 5 mg |
| lactose | 50 mg |
| corn starch | 25 mg |
| talcuum | 15 mg |
| magnesium stearate | 5 mg |
| | 100 mg |

EXAMPLE 24

| Ointment | |
|---|---|
| Compound of Example 6 | 0.020% by weight |
| methylparabene | 0.025% by weight |
| propylparabene | 0.015% by weight |
| sodium lauryl sulfate | 1.000% by weight |
| propylene glycol | 12.000% by weight |
| stearyl alcohol | 25.000% by weight |
| white petrolatum | 25.000% by weight |
| purified water | 37.000% by weight |

We claim:

1. A compound of the Formula (I)

$$\{CH_3—(CH_2)_{29}—O—\}_m—R \qquad (I)$$

wherein
m is 1 or 2, and
if m is 1, then
R is 1-lactosyl, 1-genciobiosyl, 1-laminaribiosyl, 1-cellobiosyl, 1-maltosyl, 1-maltotriosyl, 1-maltotetraosyl, 1-maltopentaosyl, 1-maltohexaosyl, 1-maltoheptaosyl or 1-maltooctaosyl or an acetylated derivative thereof; and
if m is 2, then
R is 1,8-di-(beta-D-glucopyranos-6-yloxy-1-yl)-3,6-dioxaoctane, 1,5-di-(beta-D-glucopyranos-6-yloxy-1-yl)-3-oxapentane, 1,2-di-beta-D-glucopyranos-6-yloxy-1-yl)-ethane, 1,8-di-(2,3,4-tri-O-acetyl-beta-D-glucopyranos-6-yloxy-1-yl)-3,6-dioxaoctane, 1,5-di-(2,3,4-tri-O-acetyl-beta-D-glucopyranos-6-yloxy-1-yl)-3-oxapentane, or 1,2-di-(2,3,4-tri-O-acetyl-beta-D-glucopyranos-6-yloxy-1-yl)-ethane.

2. A compound according to claim 1 wherein m is 1 and
R is selected from the group consisting of 1-cellobiosyl heptaacetate, 1-lactosyl heptaacetate, 1-maltosyl heptaacetate, 1-matotriosyl decaacetate, 1-maltotetraosyl tridecaacetate, 1-maltopentaosyl hexadecaacetate, 1-maltohexaosyl nonadecaacetate, 1-maltoheptaosyl docosaacetate, or 1-maltooctaosyl pentacosaacetate.

3. A compound according to claim 1 wherein m is 2 and
R is 1,8-di-(beta-D-glucopyranos-6-yloxy-1-yl)-3,6-dioxaoctane or 1,8-di-(2,3,4-tri-O-acetyl-beta-D-glucopyranos-6-yloxy-1-yl)-3,6-dioxaoctane.

* * * * *